(12) United States Patent
Lapszynski

(10) Patent No.: US 9,403,213 B2
(45) Date of Patent: Aug. 2, 2016

(54) PREPARATION OF FORMED ORTHOPEDIC ARTICLES

(75) Inventor: John Lapszynski, Oak Ridge, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1622 days.

(21) Appl. No.: 12/514,342

(22) PCT Filed: Nov. 13, 2007

(86) PCT No.: PCT/US2007/023949
§ 371 (c)(1),
(2), (4) Date: Aug. 11, 2010

(87) PCT Pub. No.: WO2008/063526
PCT Pub. Date: May 29, 2008

(65) Prior Publication Data
US 2010/0297462 A1    Nov. 25, 2010

Related U.S. Application Data

(60) Provisional application No. 60/858,607, filed on Nov. 13, 2006.

(51) Int. Cl.
*B22F 3/11* (2006.01)
*A61F 2/30* (2006.01)
(Continued)

(52) U.S. Cl.
CPC .............. *B22F 3/11* (2013.01); *A61F 2/30771* (2013.01); *B22F 1/0059* (2013.01); *B22F 3/24* (2013.01); *A61F 2/3094* (2013.01); *A61F 2/34* (2013.01); *A61F 2/36* (2013.01); *A61F 2/389* (2013.01); *A61F 2/3859* (2013.01); *A61F 2/4455* (2013.01); *A61F 2002/30013* (2013.01);
(Continued)

(58) Field of Classification Search
CPC ............................ A61F 2/30771; B22F 3/225
USPC ........................................................ 419/26, 2
See application file for complete search history.

(56) References Cited

U.S. PATENT DOCUMENTS 2,332,737 A   10/1943  Marvin et al.
3,114,961 A   12/1963  Chambers et al.
(Continued)

OTHER PUBLICATIONS

International Search Report, PCT/US2007/23949, dated Jan. 31, 2008.
(Continued)

*Primary Examiner* — Jessee Roe
*Assistant Examiner* — Christopher Kessler
(74) *Attorney, Agent, or Firm* — Lerner, David, Littenberg, Krumholz & Mentlik, LLP

(57) ABSTRACT

In one embodiment, the present invention may be a method of forming a porous and/or dense article from metal powder (12), including adding to a mold a first feedstock comprising an agglomerated metal powder (12) and an agglomeration agent, forming said first feedstock into a green state dense article (22); and removing said agglomeration agent. Furthermore, the present invention may include a second feedstock including an agglomerated metal powder (12), a space filling material and an agglomeration agent which may be formed into a green state porous article (21). The present invention also includes a dense and/or porous article (22 and 21) manufactured by various methods, as well as methods for creating the dense and porous feedstocks. Moreover, the present invention may include an article which may be a medical implant.

13 Claims, 2 Drawing Sheets

(51) Int. Cl.
    *B22F 1/00*     (2006.01)
    *B22F 3/24*     (2006.01)
    *A61F 2/34*     (2006.01)
    *A61F 2/36*     (2006.01)
    *A61F 2/38*     (2006.01)
    *A61F 2/44*     (2006.01)

(52) U.S. Cl.
    CPC .......... *A61F 2002/30957* (2013.01); *A61F 2002/30968* (2013.01); *A61F 2250/0024* (2013.01); *A61F 2310/00017* (2013.01); *A61F 2310/00023* (2013.01); *A61F 2310/00029* (2013.01); *B22F 2001/0066* (2013.01); *B22F 2998/10* (2013.01); *Y10T 428/12028* (2015.01)

(56) References Cited

U.S. PATENT DOCUMENTS

| | | | |
|---|---|---|---|
| 3,262,159 A | | 7/1966 | Faulkenau et al. |
| 3,362,818 A | | 1/1968 | Schwarzkopf et al. |
| 3,852,045 A | * | 12/1974 | Wheeler et al. ........ 428/566 |
| 4,179,485 A | | 12/1979 | Tritten et al. |
| 4,208,472 A | | 6/1980 | Cho et al. |
| 4,419,413 A | | 12/1983 | Ebihara et al. |
| 4,443,404 A | | 4/1984 | Tsuda et al. |
| 4,612,160 A | | 9/1986 | Donlevy et al. |
| 4,626,392 A | | 12/1986 | Kondo et al. |
| 4,644,942 A | | 2/1987 | Sump |
| 4,665,113 A | | 5/1987 | Eberl et al. |
| 4,854,496 A | | 8/1989 | Bugle |
| 5,033,939 A | | 7/1991 | Brasel |
| 5,080,672 A | | 1/1992 | Bellis et al. |
| 5,098,870 A | | 3/1992 | Claar et al. |
| 5,104,410 A | | 4/1992 | Chowdhary |
| 5,393,484 A | | 2/1995 | Seyama et al. |
| 5,641,920 A | | 6/1997 | Hens et al. |
| 5,654,106 A | | 8/1997 | Purnell et al. |
| 5,734,959 A | | 3/1998 | Krebs et al. |
| 5,766,527 A | | 6/1998 | Schildgen et al. |
| 5,848,351 A | | 12/1998 | Hoshino et al. |
| 5,853,652 A | | 12/1998 | Schildgen et al. |
| 5,879,398 A | | 3/1999 | Swarts et al. |
| 5,926,685 A | | 7/1999 | Krebs et al. |
| 5,950,063 A | | 9/1999 | Hens et al. |
| 6,008,281 A | | 12/1999 | Yang et al. |
| 6,022,509 A | | 2/2000 | Matthews et al. |
| 6,094,798 A | | 8/2000 | Seeliger et al. |
| 6,171,360 B1 | | 1/2001 | Suzuki et al. |
| 6,221,125 B1 | | 4/2001 | Soda et al. |
| 6,234,660 B1 | * | 5/2001 | Hullmann et al. ........ 366/98 |
| 6,277,150 B1 | | 8/2001 | Crawley et al. |
| 6,334,882 B1 | | 1/2002 | Aslund et al. |
| 6,391,250 B1 | | 5/2002 | Wolfsgruber et al. |
| 6,461,563 B1 | | 10/2002 | Lim et al. |
| 6,488,887 B1 | | 12/2002 | Arai et al. |
| 6,544,472 B1 | | 4/2003 | Compton et al. |
| 6,607,557 B1 | | 8/2003 | Brosnahan et al. |
| 6,641,640 B1 | | 11/2003 | Hesse et al. |
| 6,660,224 B2 | | 12/2003 | Lefebvre et al. |
| 6,660,225 B2 | | 12/2003 | Lim et al. |
| 6,669,898 B2 | | 12/2003 | Gressel et al. |
| 6,706,239 B2 | | 3/2004 | Haack et al. |
| 6,776,329 B2 | | 8/2004 | Schwarzbauer et al. |
| 6,889,852 B1 | | 5/2005 | Loncke et al. |
| 6,913,623 B1 | | 7/2005 | Zhu |
| 7,048,792 B2 | | 5/2006 | Axen et al. |
| 7,347,968 B2 | | 3/2008 | Lim et al. |
| 2001/0001640 A1 | | 5/2001 | Miller et al. |
| 2002/0104405 A1 | | 8/2002 | Haack et al. |
| 2003/0055511 A1 | * | 3/2003 | Schryver ........ A61F 2/28 623/23.5 |
| 2003/0153981 A1 | | 8/2003 | Wang et al. |
| 2005/0249625 A1 | | 11/2005 | Bram et al. |
| 2006/0002810 A1 | | 1/2006 | Grohowski |
| 2006/0129240 A1 | | 6/2006 | Lessar et al. |
| 2006/0149387 A1 | | 7/2006 | Smith et al. |
| 2006/0228247 A1 | | 10/2006 | Grohowski |
| 2007/0093912 A1 | | 4/2007 | Borden |

OTHER PUBLICATIONS

Dickey, David S., "Power and Bulk Mixing: Processes, Applications and Equipment", Apr. 19-20, 2006, Philadelphia, Pennsylvania, 364 pages.

The Universtity of Wisconsin Madison / College of Engineering Department of Engineering Professional Development, "2006 Course Connection / Your link to more than 300 continuing education courses", 8 pages.

The Universtity of Wisconsin Madison / College of Engineering Department of Engineering Professional Development, "Atomization and Spray Technology", Apr. 26-27, 2006 Madison, Wisconsin, 8 pages.

The Universtity of Wisconsin Madison / College of Engineering Department of Engineering Professional Development, "Chemical and Process Engineering Short Courses 2006", 2 pages.

The Universtity of Wisconsin Madison / College of Engineering Department of Engineering Professional Development, "Dryer Technology", Apr. 24-25, 2006, Madison, Wisconsin, 8 pages.

The Universtity of Wisconsin Madison / College of Engineering Department of Engineering Professional Development, "Industrial Crystallization Operations", May 31-Jun. 1, 2006, Madison, Wisconsin, 8 pages.

The Universtity of Wisconsin Madison / College of Engineering Department of Engineering Professional Development, "Pilot Plant and Scale-Up Methods for Industrial Mixing", Jun. 13-15, 2006, Philadelphia, Penssylvania, 8 pages.

The Universtity of Wisconsin Madison / College of Engineering Department of Engineering Professional Development, "Powder and Bulk Mixing: Processes, Applications and Equipment", Apr. 19-20, 2006, Philadelphia, Pennsylvania, 8 pages.

The Universtity of Wisconsin Madison / College of Engineering Department of Engineering Professional Development, "The Art and Science of Industrial Mixing", Mar. 21-23, 2006, Las Vegas, Nevada, May 16-18, 2006, Madison, Wisconsin, 8 pages.

* cited by examiner

PREPARATION OF FORMED ORTHOPEDIC ARTICLES

CROSS-REFERENCE TO RELATED APPLICATIONS

The present application is a national phase entry under 35 U.S.C. §371 of International Application No. PCT/US2007/023949, filed Nov. 13, 2007, published as WO 2008/063526 A1, which claims priority from the benefit of the filing date of U.S. Provisional Patent Application No. 60/858,607 filed Nov. 13, 2006, the disclosures of which are hereby incorporated herein by reference.

BACKGROUND OF THE INVENTION

The metal injection molding process, as is well known in the powder metallurgy art, uses a mold which comprises an at least one injection port through which a powder metal feedstock composition is introduced into the mold. The injection equipment then employs pressure and/or heat to fuse the powder, or powders, together to form a desired shape as per the shape of the mold cavity.

The powder metallurgy art also utilizes various other types of forming processes such as die compression, uniaxial pressing, cold isostatic pressing, hot isostatic pressing and many others. Processes such as these are used to form articles from metal powder. While processes such as metal injection molding are capable of forming very precise and nearly finished articles, the cost of the molding equipment can be very high. Conversely, processes such as die compression and cold isostatic pressing are more basic processes which can form general shapes and configurations, but which often require more involved finishing and machining processes than metal injection molding, before a final article is obtained, particularly in the case of orthopedic articles.

An agglomeration process produces clusters of powder materials with a relatively uniform size distribution, independent of the starting particle size distribution of the powder material. A number of methods exist for agglomerating powder material. Some methods might include the use of a fluid bed, spray drying, and/or pan pelletizing process.

SUMMARY OF THE INVENTION

The formed metal powder porous and/or dense article, in one embodiment, may be composed of two or more separately formulated feedstock compositions. One feedstock composition may form a dense or solid section of a desired formed metal powder porous and/or dense article. Another feedstock composition may form a porous section of the formed metal powder porous and/or dense article. The two sections may have vastly differing densities.

The feedstock which may form a dense or solid section may include, in one embodiment, substantially spherical metal powder particles. Spherical shaped particles allow for, among other advantages, tighter packing, which creates a higher density object.

The feedstock which may form the porous portion, on the other hand, may include, in one embodiment, substantially irregular shaped metal powder particles. Additionally, the feedstock which may form the porous portion may also include a space filling material which may, upon forming of the article from the feedstock, create a porous structure. The irregular shaped particles, in some embodiments, may during the forming process interlock and even deform with one another to form a green state formed article, or green article, of high strength.

The formed metal powder porous and/or dense article may be, in one embodiment, formed from an at least one feedstock wherein at least one feedstock may be an agglomerated metal powder. The metal powder may undergo an agglomeration process prior to being placed within a mold. In one embodiment, the agglomerated metal powder may include an agglomeration agent. The agglomeration agent, generally, provides for more uniform and evenly sized agglomeration clusters. Moreover, during forming processes such as, for example, metal injection molding or die compression, the agglomeration agent may act as a lubricant during insertion of the agglomerated powder into the mold and also during the actual forming process. In the case of the feedstock of the porous section, the agglomerated metal particle clusters may be, in one embodiment, substantially the same size as the space filling material. In other embodiments, the space filling material may be either larger or smaller than the agglomerated particle clusters.

Agglomerated metal powders are particularly beneficial in the manufacture of articles that include a solid load bearing, or articulating portion, in combination with a highly porous region, which may be a location for fixation to living bone or soft tissue. As the dense and porous portions are formed, the powders that make up the solid and porous portions can be formed simultaneously and consolidated simultaneously as a result of mechanical and/or chemical processing. The agglomerated powders are sequentially filled into the mold, formed, and sintered in a final operation. Space filling material and any additional materials, such as agglomeration agents, are removed chemically or thermally prior to sintering.

In one embodiment, the present invention may be a method of forming a porous and/or dense article from metal powder, including adding to a mold a first feedstock comprising an agglomerated metal powder and an agglomeration agent; forming said first feedstock into a green state dense article; and removing said agglomeration agent. Furthermore, the step of adding to the mold may further include adding a second feedstock including an agglomerate metal powder, an agglomeration agent and a space filling material. Also, the step of forming the green state may include simultaneously forming the first and second feedstocks in a green state dense and porous article. Moreover, the step of removing the agglomeration agent may further include removing the space filling material.

In another embodiment, the present invention may be a method of forming a porous and/or dense article from metal powder, including adding to a mold a first feedstock comprising an agglomerated metal powder and an agglomeration agent; forming said first feedstock into a green state dense article; and removing said agglomeration agent. Furthermore, such an embodiment may further include, after the step of forming a first feedstock into a green state dense article, the steps of, adding to the mold a second feedstock including an agglomerated metal powder, an agglomeration agent and a space filling material, and forming a green state article comprising said green state dense article of said first feedstock and said second feedstock.

In a further embodiment, the present invention may include a porous and/or dense article made by the process of adding to a mold a first feedstock comprising an agglomerated metal powder and an agglomeration agent and a second feedstock comprising an agglomerated metal powder, an agglomeration agent and a space filling material; simultaneously forming the first and second feedstocks into a green state dense and porous article; and removing the space filling material and the agglomeration agent from the green state dense and porous article.

In still another embodiment, the present invention may include a porous and/or dense article made by the process of adding to a mold a first feedstock comprising an agglomerated metal powder and an agglomeration agent; forming the first feedstock into a green state dense article; adding to the mold a second feedstock comprising an agglomerated metal powder, a space filling material and an agglomeration agent; forming a green state dense and porous article comprising said green state dense article of said first feedstock and said second feedstock; and removing the space filling material and the agglomeration agent from the green state dense and porous article.

In yet another embodiment, the present invention may include a green article including a first portion comprising an agglomerated metal powder and an agglomeration agent and a second portion comprising an agglomerated metal powder, a space filling material and an agglomeration agent.

In yet a further embodiment, the present invention may include a method of making a feedstock of metal powder for use in forming a dense and/or porous article, including combining a metal powder and an agglomeration agent to form an agglomerated powder, and combining the agglomerated powder and a space filling material.

The disclosure of the present invention herein may be used in any application where there is a need for a porous and/or dense article. However, for ease of explanation, the present invention will be disclosed as to a medical implant, and more specifically, an acetabular cup, a femoral hip stem, a femoral knee component, a tibial base plate, a spinal fusion or stabilization device, or the like. As to a medical implant, the metal injection molded porous and/or solid article may display high porosity level, high mechanical strength and biocompatibility.

DESCRIPTION OF INVENTION

Figure 1:
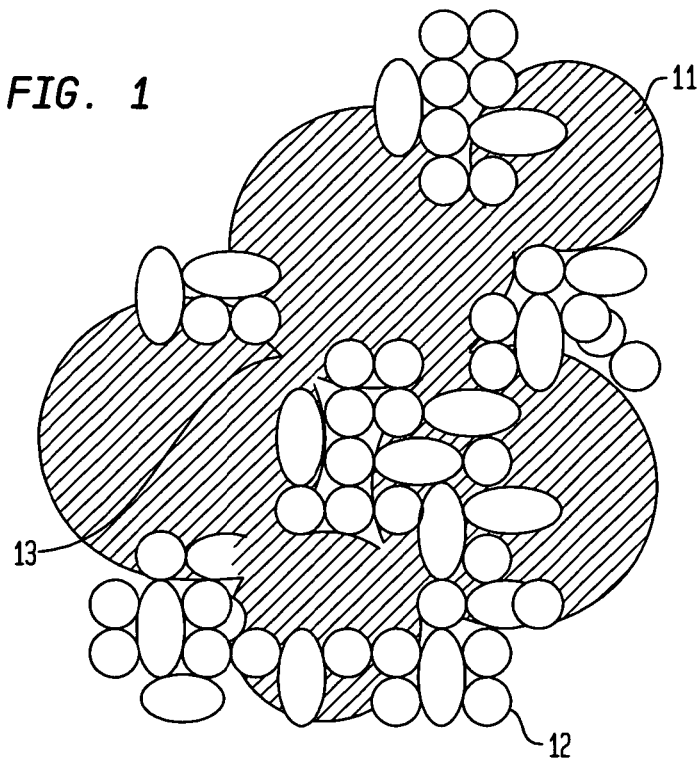
FIG. 1 illustrates interconnecting porosity of a porous portion of a porous and/or dense article of one embodiment of the present invention.

The disclosed invention relates to a novel process for creating an improved formed metal powder porous and/or dense article applicable to, for example, the field of medical implants. This process, as one skilled in the art would recognize, may be applicable to many industries in which powder metal particles may be used in a forming process.

Generally speaking, in one embodiment, the formed metal powder porous and/or dense article (hereinafter referred to as "formed article") may be, in one embodiment, formed through the application of pressure inside a mold. The formed article is then removed from the mold, while in a "green state." The formed article in the green state may be subsequently machined and further processed including for example, removing of additional material, debinding, leaching, sintering or other further additional processes, to create a finished article. The actual further machining and/or processing of a formed article in a green state may depend on, for example, the materials used, the molding process used, any additional materials used in the preparation of the green state formed article, or the green article, and the like. These further processing and machining steps will be discussed below.

In one embodiment, the formed article may include a dense feedstock including a metal powder. Additionally, the dense feedstock may include an additional material. A porous feedstock may also include a metal powder, and additionally may include a space filling material and may further include an additional material.

One example of an additional material added to either the dense or porous feedstocks, or both, may be a binder. If a binder is used, the formed article may then be machined initially while still in the bound state. However, initial machining may also occur subsequent to de-binding and sintering. Other additional materials may include, but are not limited to, flow enhancing materials, lubricants, adhesives, agglomeration agents, or the like.

The dense feedstock may be composed of pure substantially spherical metal powder and, in one embodiment, a small amount of an additional material. The additional material may serve various functions, such as, for example, to allow for ease of insertion of the metal powder into the mold cavity, or to assist in the formation of an agglomerated metal powder prior to insertion into the mold cavity, discussed below. Maintaining purity in this feedstock composition, aside from the aforementioned additional material, may ensure tight packing of the metal powder to create a dense solid article. In such an embodiment, the substantially spherical shape of the metal powder may ensure tight packing of the metal powder.

In another embodiment of the present invention, porous feedstock may be composed of metal powder and a space filling material. Again, in one embodiment, a small amount of additional material may also be added to allow for greater efficiency and performance during, for example, insertion of the feedstock into the mold cavity or in preparation of an agglomeration of the metal powder prior to insertion into the mold cavity. The metal powder may be of the same metal as the dense feedstock composition or may be of a different metal. Even though the metal powder of the porous feedstock may be the same metal as the metal powder of the dense feedstock, the metal powder of the porous feedstock may be of a substantially irregular shape, while the metal powder of the dense feedstock may be of a substantially spherical shape.

The metal powder of both feedstock compositions may be composed of any metal desired. In the example of medical implant articles, biocompatible or implantable metals may be used. Specifically, the metal powder used in this invention may be titanium, although any other suitable metal is contemplated. Titanium is biocompatible and has a very high strength to weight ratio which makes it highly desirable for medical implant material. Other materials which may be used within the parameters of the present invention include, for example, cobalt chrome, stainless steel, or any other biocompatible or implantable material.

Titanium is well known as a highly volatile metal, which has inhibited its use in metal powder forming processes, particularly in metal injection molding processes. Drawbacks from using titanium are usually contributed to contamination from, for example, contact with oxygen. Contamination of titanium may result in a change in its chemistry which could lead to a change in its mechanical properties, including a loss in strength. This is especially true when using high grades of titanium, such as is required for medical implants. However, the present invention provides a method of manufacturing formed articles from titanium such that the manufactured article does not suffer from the drawbacks to using titanium in a forming application.

In accordance with one embodiment of the present invention, the metal powder particles of the porous feedstock may have an irregular shape, rather than the substantially spherical shape which may be more advantageous when used in the dense feedstock. The irregular shape of the metal powder particles provide for a formed article with added strength properties, not only when in the green state, but also throughout the sintering process after the space filling material has been leached out. The irregular shape of the metal powder particles, when pressed in the mold, will interlock with one another. The mechanical interlocking between metal powder particles results in increased bonding strength. This is particularly beneficial when the formed article is removed from the mold while in the "green state," prior to sintering. The interlocking allows the debinding (if a binder is used), leaching (of the space filling material) and sintering processes to be conducted on the porous article without the requirement of having the article remain in the mold. The strength obtained from the irregularly shaped metal powder particles may allow for a porous feedstock to be used that does not require a binder in the mixture.

Typically, a formed article in the "green state" is very fragile and thus requires pre-sintering before a de-binding process, leaching process, or other finishing process, can be performed. However, using irregularly-shaped metal powder particles may eliminate the need for pre-sintering, thus cutting down on production time and costs.

A typical problem with using irregular shaped metal powder particles in a forming process is the flow of the metal powder feedstock composition into the mold cavity. The irregular shape does not flow as smoothly as the spherical particles, thus creating problems when transferring the irregular shaped metal powder particles into the mold.

This problem may, in one embodiment, be resolved through the use of an additional material which has properties that allow for easier flow into the mold, such as a flow enhancing material. This flow enhancing material serves to smoothen the insertion of the metal powder into the mold and create a more reliable and efficient insertion process.

The space filling material, in the porous feedstock composition, may be any substance that has properties sufficient to give a formed metal powder a porous quality. As can be seen in the attached FIG. 1, the space filling material creates major pores 11 which are surrounded by metal powder 12. Moreover, in the locations where the individual space filling material may touch each other, or may be in close proximity to each other, interconnecting porosity 13 may result.

In accordance with the invention, the space filling material may be, but is not limited to, salts (calcium chloride, phosphates), hydroxyapatite, polyethylene beads, Mannitol or other sugars. The space filling material chosen depends upon, for example, the final product design requirements, the processing methods used or the reactivity of the materials. Specifically, the type of space filling material chosen may affect the level of porosity and, if present, the interconnecting porosity of a porous section of the formed article. As will be discussed below, the space filling material, once the article is formed, may be removed through any known process such as leeching with a solvent, thermodegradation, during the sintering process, or the like.

One type of additional flow enhancing material which may be included in either or both of the feedstock compositions, may be a lubricant which may allow the particular feedstock composition to have greater homogeneity and to be more easily introduced into the mold. An example of this lubricant may be, but is not limited to, polyethylene glycol (PEG). The material chosen depends upon, for example, the final product design requirements, the processing methods used or the reactivity of the materials. The flow enhancing material in the present invention exists in a small amount, in some embodiments less than 0.1% by volume of the entire feedstock composition.

Another flow enhancing material, found, if at all, in the dense feedstock, may be a binder. The binder used will depend on the particular desired characteristics of the dense portion of the formed article. The possible binders used in this invention are similar to those already known in the art. Generally, the purpose of the binder is to create an additional cohesive force between the substantially spherical metal powder particles. As will be further discussed below, if an agglomeration agent is used, and thus, the metal powder particles are agglomerated prior to insertion into the mold, then a binder may not be included in the process.

In another embodiment, either feedstock composition may use agglomerated metal powder which may enhance the homogeneity and usefulness of the feedstock metal powder. The use of agglomerated metal powder may allow for independent control of particle size range of the agglomerated metal powder for blending, handling, and filling (of the mold) while retaining a smaller, more favorable powder size for compaction and sintering. A narrow size range of large agglomerated metal powder may simplify the blending operation for the porous portion, the filling operations for the dense portion and the porous portion, and may allow for partial forming of each portion prior to full forming, through compaction or otherwise, of the entire article at a higher pressure.

Throughout this example, titanium will be used, though any biocompatible or implantable metal may be used. Titanium, however, may benefit from this process more than other metals because of its high reactivity, which will be explained further below. The agglomerated titanium is essentially titanium powder particles grouped together to form thicker, larger, clusters. This may be seen in FIG. 1, which shows metal powder in clusters 12. The agglomerated titanium powder promotes thicker and more useful clusters of metal powder. Agglomerated titanium may be produced using any agglomeration process known in the art. For example, the titanium of the present invention may be agglomerated using a fluidized bed. Typically, a fluidized bed process causes the solid metal powder, resting on a flat plate, to act as a liquid through the introduction of pressurized gas, which may then be passed through the powder particles. The pressurized gas is passed up through holes in the plate which causes the powder particles to become suspended within the pressurized gas. This process may occur at any temperature; however elevated temperatures have the most beneficial impact on the process. The gas may be pressured such that it suspends the powder particles above the bed.

Titanium powder may be agglomerated in any suitable manner, including, for example, the use of adhesives, or agglomeration agents. Agglomeration agents may be applied to the titanium powder, for example, while the powder is suspended in the fluidized bed. The agglomeration agent may be sprayed or atomized over the powder to cause the powder particles to stick together and form clusters. In the example of the fluidized bed, the spray rate of the agglomeration agent, and the nozzle pressure, may be adjusted such that there is not excessive accumulation of agglomeration agent spray such that it creates "blobs" on the metal powder. Thus, the spray rate and nozzle pressure may be adjusted to maintain a mist or atomization over the metal powder. Moreover, within the parameters of this example, the compressed gas may be heated to dry the particles and adhesives. For example, as an illustration of the fluidized bed process, the compressed gas temperature may be adjusted such that the metal powder particles, which may be in the form of clusters, dry as they settle to the bottom of the fluidized bed. The specific parameters of the fluidized bed, compressed gas and possible agglomeration agents may be adjusted to generate appropriate agglomerate sizes, strengths and/or yields.

Agglomeration agents that are water soluble or heat soluble may be used. For example, in one embodiment, the agglomeration agent may be polyethylene glycol (PEG 20K) or the like, which may be present in solution with water, or the like, in a concentration which may be adjusted to maintain a viscosity level that allows for a desired spray rate and nozzle pressure. The viscosity level may change with the amount of PEG in the solution, for example, the more PEG which is in solution, the higher the viscosity of the solution.

Further to this embodiment, the amount agglomeration agent, within the feedstock, may be as minimal as possible so as to occupy a minimum amount of space between the metal particles. On the other hand, the agglomeration agent may be present in a sufficient amount in the feedstock so as to maintain strong green state properties. The titanium powder clusters 12, as a result, may be closer in size to the larger space filling material, which allows for better mixing and packing in the porous feedstock composition. Thus, in one embodiment, the agglomerated titanium clusters 12 may be substantially the same size as the major pores 11, which may be formed by the space filling material.

The agglomerated titanium may be of a relatively precise mixture and consistency. While the agglomerated titanium must be strong enough to remain together in clusters during mixing, the bonding must also be weak enough such that the titanium clusters may be moved around the space filling material during the forming process.

As seen in FIG. 1, in certain embodiments the agglomerated metal powder 12 may surround the space filling material, forming the major pores 11, with interconnecting passages or porosity 13, such that the metal powder particles 12, in the form of agglomerated metal clusters, form walls around the space filling material while still maintaining interconnecting porosity 13. The agglomerated metal clusters 12 should not be strong enough to break the space filling material. Moreover, the agglomerated titanium 12 must be strong enough to survive the mixing process, but weak enough that they may be manipulated once inside the mold to substantially fit into the voids around the space filling material.

Though the agglomerated metal clusters 12 have a limited consistency range, the desired consistency is relatively reproducible within a specified range. In one embodiment, the specified range may be where the agglomerated metal clusters 12 are roughly of similar size to the space filling material, and are thus roughly of similar size to the major pores 11. For example, if the desired pore 11 size is 100 to 800 μm, then the agglomerated metal clusters 12 should also be produced such that the clusters 12 are roughly 100 to 800 μm. For example, hydride-dehydride (HDH) titanium powder, for use in the agglomeration process, may have an average particle size of about 25 μm to about 100 μm. Particles of this size, upon undergoing agglomeration, may produce agglomerated clumps of about 800 μm or less. However, for the application of this present invention as to the field of medical implants and other various formed metal powder porous and/or dense articles, the agglomerated clusters may be of a size of about 250 μm or less.

The agglomerated metal clusters 12 create a packing arrangement in which the titanium clusters 12 may be manipulated to surround the space filling material. Through this packing arrangement, the agglomerated metal clusters 12 create an "eggshell" structure around the space filling material particles. These eggshells are interconnected to each other, and interconnecting passages 13 between them form the desired level of interconnectivity.

Agglomerated metal clusters of substantially spherical shaped metal particles, as in the dense feedstock, may form a more cohesive dense portion during the forming process. The agglomerate metal clusters, upon undergoing a forming process, may tightly pack together to form a highly dense portion of the formed article. Moreover, the use of agglomerate metal clusters, which may include an agglomeration agent, may not require the presence of a binder in the feedstock composition, since the agglomeration agent may be sufficient to maintain cohesion among the agglomerated metal clusters and thus maintain a highly dense and strong dense portion of the formed article that is of sufficient strength to undergo further processing and machining without the need to remain within the mold.

The use of agglomerated metal may provide numerous benefits in subsequent processes such as, for example, filling of the mold, blending with other materials (i.e., space filling materials), and forming processes (for example, compaction and molding processes) where the agglomeration agent, if correctly chosen, may act as a flow enhancing agent or lubricant and also may prevent the powder material from settling. Generally, the agglomerated metal may be beneficial in maintaining and improving uniformity of the feedstock and/or the formed article.

In one embodiment, the present invention may include manufacturing the formed article using a process which may apply pressure to form the at least two metal powder feedstock compositions into the dense and/or porous article. The forming process may use various techniques and various sequences in order to obtain the formed article. As a generalization, any forming process disclosed herein uses some type of mold within the cavity of which the formed article is produced. As used herein, a mold may be, for example, a mold in a cold isostatic pressing or metal injection molding process, or may also be a die cast in a die compression process, or the like.

For example, the forming process may be completed inside a single mold incorporating both feedstock compositions, or the forming process may be completed using two different molds, one for each feedstock. Moreover, the forming process may use a dense substrate onto which the porous feedstock is formed. The present invention may be used in any type of forming process.

For example, in yet another embodiment, a two-stage expanding mold may be used, in a metal injection molding process, to accommodate a two shot forming process. The mold design may be such that the first shot, or stage one, accepts the dense feedstock composition and forms it to a pre-determined, desired dimension and shape. Upon completion of the first stage, the mold may then expand through mechanical means in order to create additional room in the mold. The expansion of the mold allows for injection of the porous feedstock composition. The porous feedstock is then formed together with the formed section of dense feedstock. The addition of the dense and porous feedstocks may be in any order, such that the dense feedstock may be the first feedstock introduced and the porous feedstock may be the second feedstock introduced, or vice versa. In one embodiment, the agglomerated feedstock compositions may also be used in this process. This process may further be automated such that the entire two-step forming process is completed without any human interaction with the metal injection molding device.

In a further embodiment, and as a further example of the possible types of forming processes which may be used within the present invention, a die set compression process may be used. In this example, the mold may be a die cast. As in the metal injection molding process, either the dense or porous feedstock compositions may be initially added to the die cast. The die may then compress the first added feedstock. Then, the die may be raised to an even higher level than its initial position to allow insertion of the second added feedstock. Then, the die is compressed again to form the complete formed article. Alternatively, both feedstocks may be added to the die cast at the same time, and compressed simultaneously to form the formed article.

In an additional embodiment, the forming process may include a high velocity compaction mold. A high velocity compaction mold may use a combustion driven press to form the formed article. The combustion driven press forms the feedstocks using a high pressure caused by the high velocity of the press. The resulting formed article has a high green strength which requires less machining and processing to create the finished formed article. For example, since the formed article has such high green strength, and thus, the density of the formed article is nearly at a level sufficient for a finished article, less sintering is required. As is known to those skilled in the art, metals such as titanium alloy, when undergoing a sintering process, can undergo undesirable chemical alterations due to, for example, phase transformation. Thus, if the sintering time, and temperature, can both be lessened, the possibility of the titanium alloy undergoing phase transformation or other chemical degradation can be minimized.

For example, when combining a dense material of titanium alloy with a porous commercially pure titanium structure, dimensional changes of the formed powder article during sintering may be a concern, especially since differences in powder size, shape and chemistry make their consolidation, during the sintering process, as a function of temperature different. Consolidation of one layer at a different time and rate relative to the other, on the other hand, may lead to issues with dimensional control due to warping or issues with strength due to interfacial rifts. Utilizing powders and formation processes, such as high velocity compaction, that result in a high green density minimizes these changes. For example, formation of angular Ti-6Al-4V powder at 75 tsi (tons/square inch) results in 85% green density and a resultant sintered strength of 66 ksi while formation of the same powder at 150 tsi results in 94% green density and a resultant sintered strength of 115 ksi. Both parts were consolidated below the beta transis of the material, resulting in retention of the fine alpha-beta distribution within the sintered solid. These results demonstrate the ability to utilize compaction pressure as a means to mechanically consolidate powders prior to thermally consolidating them. As a result, high velocity compaction, and other similar processes, may provide numerous benefits to the present invention, including: powders of different compositions may be consolidated, even if their thermal consolidation takes place at different temperatures; articles may exhibit less distortion and shrinkage as a result of thermal consolidation; and articles may be consolidated at lower temperatures, lower than beta transis, therefore retaining favorable distribution of phases found in the raw material.

Other possible forming processes which may be used in the present invention may be, for example, uniaxial pressing, cold isostatic pressing, multi-strike compression (multiple compressions on a single batch of feedstock forming a denser article after each stroke) and any other process which is capable of forming metal powder formed articles. The type of forming used in the present invention may depend upon the type of article to be formed, the materials used, the level of detail required on the formed article, and the type of final machining and processing processes the formed article may undergo. For example, the metal injection molding process is fairly expensive, but the formed article, typically, will be a nearly finished article, requiring little additional machining. This is because the metal injection molding process is highly accurate. Cold isostatic pressing, or die cast compression, on the other hand, are more rudimentary processes which may produce a formed article requiring substantial additional machining and processing, but either process is relatively inexpensive. Furthermore, high velocity compression, as well as cold isostatic pressing, both produce a formed article which, in the green state, have high strength properties, which can be beneficial in that less sintering, or a lower sintering temperature, may be required.

Additionally, in certain embodiments where the dense and porous feedstocks are added to the mold, and then formed simultaneously, the first added feedstock may be tamped prior to the addition of the second added feedstock. The tamping process may minimize the combining or mixing the first and second added feedstocks. Some amount of combination or mixing may be inevitable, which may be beneficial to the composition of the formed article. For example, a minimal amount of mixing between the first and second added feedstocks may provide a better porosity gradient than if the dense and porous portion were formed individually. The gradient, aside from creating a smooth transition from the dense to porous portions, may also provide for a greater strength of bonding between the dense and porous portion.

The forming process culminates in the production of a formed article in a "green state." A green state article is one that is freshly formed and has not been sintered or finished in any way. At this point, the formed article still may have any additional materials (i.e., binder, lubricant, adhesive, agglomeration agent, etc.) in the dense and/or porous portions, and/or space filling material within the porous portion.

The formed article which may be produced from the present invention is stronger than other articles produced through other processes. Since, in some embodiments, the forming may be conducted using two powder feedstock compositions, formed simultaneously, the two portions of the article bind together at a flush interface. Therefore, at the interface, the two sections may form a continuous surface with decreased stress concentrations therein. This creates a formed article with stronger mechanical properties.

Figure 2:
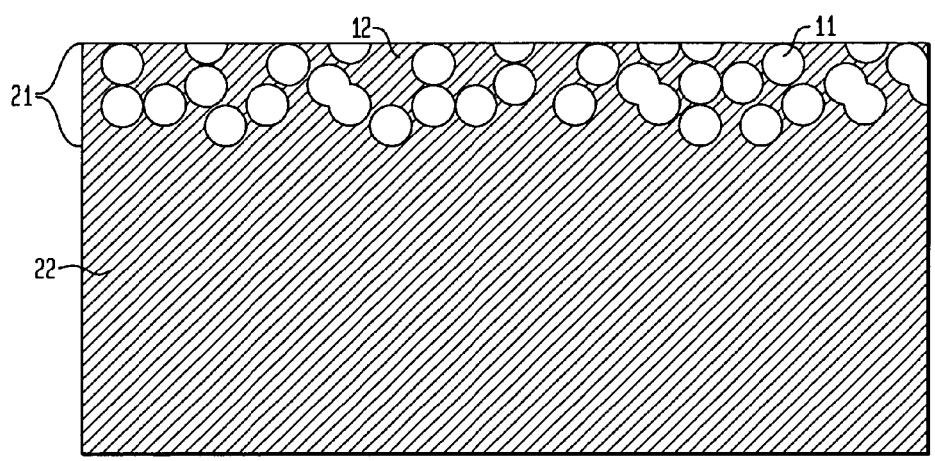
FIG. 2 illustrates a cross-section of a porous and/or dense article of one embodiment of the present invention.

This embodiment, as seen in FIG. 2, may create a flush interface between porous portion 21 and dense portion 22. The formed article produced by this embodiment may have no indication of an interface between the two portions. Instead, the formed article of this embodiment may have a smooth transition from the dense portion 22 to the porous portion 21. As seen in FIG. 2, there may be no indication of a transition point between the dense portion 22 and the porous portion 21, such as a notch or crease, which could cause a decrease in mechanical strength properties. Moreover, as discussed above, in an embodiment where the porous and dense portions are formed simultaneously, any intermixing between these two feedstocks during the forming process may provide additional strength between the porous and dense portions, as well as the aforementioned porosity gradient, such that the transition point from one portion to the other is nearly indistinguishable, and may further not be present.

The green state article then may proceed through a de-binding, removing and leaching phase in which the additional materials and space filing material are separated or removed from the formed article, creating a "brown state." The dense portion of the formed article, in embodiments where a binder was used, may undergo a de-binding process performed in various manners, a couple of which include water de-binding, chemical de-binding or thermo de-binding. The de-binding process chosen is dependent upon what type of binder was used. Additionally, such removing processes may be used to remove other additional materials which may have been added, such as flow enhancing materials, agglomeration agents or lubricants, for example.

The porous portion of the formed article may undergo a leaching process, as is well known in the art, to remove the space filling material from the interconnecting pores. For example, if a salt is used as the space filling material, the formed article may be placed in a water bath which would dissolve the salt thereby removing it from the interconnecting pore structure. The method of leaching is dependent upon the type of space filling material used and the amount of porosity of the formed article.

In some embodiments, the de-binding, removing and/or leeching processes may be conducted simultaneously, depending on the additional materials and space filling materials which are used. Therefore, if all the included materials are water soluble, a single water bath may be used to remove both materials. Conversely, if the materials are thermo-degradable, then a single thermo de-binding process may be sufficient to remove all materials from the formed article.

After the de-binding and leaching processes are complete, the formed article may be sintered, typically in a single process. A single sintering process may be used because the entire formed article is still in a green state, or a brown state if the article has been de-bound and leached, and thus the solid and porous portions thereof will consolidate and shrink at a similar rate throughout. This will allow for superior bonding potential between the two feedstock composition portions. This is in contrast to a forming process in which a powder feedstock composition is formed onto a finished solid substrate. The solid substrate is already sintered and condensed, while the powder feedstock section is not. Thus, in this situation, bonding strength would be compromised because one layer is shrinking and condensing during the sintering process while the other layer remains largely unchanged.

As discussed above, when a forming process such as high velocity compaction is used to form a formed article, the sintering process may be conducted for less time and/or at a lower temperature. This is because this type of forming process forms an article with very high green strength and high density, nearly to the point of that required for a finished article. Additionally, the use of small particle size for the powder in combination with high velocity compaction may result in even higher green densities and allows final sintering to be performed at times and temperatures that result in better final mechanical properties, i.e., lower temperatures and less time. Thus, less sintering is required to condense the formed article to a density required for the finished formed article. This is particularly beneficial when metals such as titanium are used which can chemically degrade during the high temperatures and exposure to oxygen during the sintering process. Thus, if the sintering temperature and time can be minimized, the opportunity for the titanium to degrade may also be minimized.

The formed article may be machined either before or after sintering. Thus, the article may undergo machining, while the article is in a green state. Various machining techniques may be performed on the formed article. Machining may be required, for example, if article forming conditions require specific gating, venting or other dimensioning. Specifically, by way of example, a formed article may be machined to create a certain level of surface roughness, at both the macroscopic and microscopic levels, on the formed article which may enhance bone growth. A further example may be to create "barbs" on the surface of the implant which serve as an additional anchor into the appropriate bone.

As a result of this process, the formed article may be net shape or near net shape with open celled interconnecting porosity of acceptable size and volume. The level of interconnecting porosity is dependent upon the packing, and interlocking, of the irregular shape metal powder particles and the space filling material. When in the mold, and under pressure, the porous feedstock composition is arranged such that the smaller metal powder particles deform, interlock, and pack around the larger space filling material. In embodiments including agglomerated metal clusters, particularly in the porous feedstock, the agglomerated metal clusters may shape to surround the space filling material during the forming process.

In one embodiment, as an example, an at least 60% porosity level may be achieved in the highly-connected open-celled porous portion of the formed article with major pore sizes preferably between 200-800 µm. Additionally, the interconnecting porosity, where present, may be roughly 180 µm. This level is possible, while still maintaining necessary chemical and mechanical properties, to assure sufficient mechanical strength, because of the interlocking of the irregular shape metal powder and the forming process. The disclosed processes may create a co-formed porous and/or dense formed article that is entirely in the green state and thus will have greater strength during the sintering process, despite the high porosity level.

Moreover, the resulting interconnecting porosity may allow for additional preparation of the implant for implantation. In one embodiment, a 3-D calcium phosphate coating, also known as a periapatite ("PA") coating, disclosed in U.S. Pat. Nos. 5,164,187 and 5,188,670, may be applied to the porous portion of the formed article through the use of a liquid bath. In this embodiment, submerging the article into the liquid bath allows the PA to be introduced into the interconnecting porosity. This process produces particularly beneficial results when the porosity is heavily interconnected, which can only be accomplished by the above invention. Applying the PA coating, in accordance with one embodiment, to a porous article allows for a greater inundation than a mere surface coating by spray or brush.

In some embodiments, the formed article may include more than just two layers, for example, and may include a central dense portion and two outer porous portions on either side of the dense portion. Using this type of formed article, in some embodiments, an additional polymer element may bind to one of the porous portions of the formed article. The use of a porous metal powder layer to secure a polymer layer within the porosity is disclosed in U.S. Patent Publication No. 2007/0142914, entitled "Laser-Produced Porous Surface," the entirety of which is incorporated by reference herein. Embodiments such as these may include non-interconnecting porosity, which may provide added structural benefits as well as preventing the polymer, during application, to leech from the specific attachment location. Of course, it is acknowledged that non-interconnecting porosity may occur in formed articles with any number of portions, as the non-interconnecting element occurs only in a porous portion. For example, in one embodiment, the present invention may relate to a method of forming an implant having a porous tissue ingrowth structure and a bearing support structure. The method may include depositing a layer of a metal powder onto a substrate, the metal powder layer having a first surface and a second surface. A flowable polymer may then be placed into contact with the second surface of the metal powder. The polymer is cooled such that the flowable polymer adheres to the second surface of the structure. An example of a polymer which may be used within the scope of this example may be polyethylene, although any flowable, biocompatible and implantable polymer known in the art may be used.

Furthermore, embodiments such as these may include placing a metal powder formed article, such as those produced using the methods disclosed herein, into a cavity of a mold and depositing a polymer onto a surface of the formed article within the cavity of the mold. The step of placing a flowable polymer in contact with the surface of the formed article may include applying pressure and heat to the polymer in the cavity of the mold. The step of placing the flowable polymer in contact with the surface of the formed article may include transferring the flowable polymer onto the surface. The step of placing the flowable polymer in contact with the surface of the predetermined structure may include placing the surface of the formed article adjacent a polymer structure, applying heat to the polymer structure and allowing the polymer structure to engage the predetermined structure. The formed article may include an outer layer, an intermediate layer and an inner layer, the outer layer and the inner layer being relatively porous and the intermediate layer being relatively dense such that the flowable polymer cannot substantially leech through the intermediate layer from the inner layer to the outer layer. The outer layer has a porosity approximately between 60% to 80% and the inner layer has a porosity approximately higher than 80%. The outer layer may have a pore size distribution in the range of 80 µm to 800 µm and the inner layer may have a pore size distribution higher than approximately 800 µm.

Furthermore, such embodiments may also include a medical implant including a metal insert having a bone ingrowth structure, an intermediate structure and a bearing support structure, the bone ingrowth structure having a porosity sufficient to promote bone ingrowth. The implant also includes a bearing surface formed from a polymer material, the bearing surface being attached to the bearing support structure. The intermediate structure has a porosity sufficient to inhibit the polymer material from translating through the bearing support structure to the bone ingrowth structure. The intermediate structure may be designed to facilitate a specific stiffness characteristic to an overall construct and/or include two barrier layers and a bridging section. As stated above, the porosity of this example may be non-interconnecting to ensure the polymer layer does not leech away from its point of attachment.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

The invention claimed is:

1. A method of forming a brown state article, having at least a porous portion, from metal powder, comprising:
    adding to a mold a first feedstock comprising an agglomerated metal powder, an agglomeration agent and a space filling material, wherein said agglomerated metal powder of said first feedstock comprises clusters of irregularly shaped metal powder, the space filling material having a size which is equal in size to the clusters;
    forming said agglomerated metal powder of said first feedstock around the space filling material into the porous portion of a green state article, wherein said agglomerated metal powder is sufficiently weak such that said clusters of agglomerated metal powder interlock, pack, and deform with one another to fit into voids and surround the space filling material; and
    removing said agglomeration agent and said space filling material to form the porous portion of the brown state article.

2. The method of claim 1, wherein said step of adding to said mold further comprises adding a second feedstock comprising an agglomerated metal powder and an agglomeration agent, and wherein said step of forming said porous portion further comprises simultaneously forming said first and second feedstocks into the porous portion and a dense portion, relative to the porous portion, of the green state article.

3. The method of claim 2, comprising the further step of machining or processing said brown state article having the dense and porous portions into a medical device.

4. The method of claim 2, wherein said second feedstock forms the dense portion and said first feedstock forms the porous portion.

5. The method of claim 4, wherein the step of simultaneous forming creates a flush interface between the dense portion and the porous portion.

6. The method of claim 1, further comprising, after the step of forming said first feedstock into the porous portion, the steps of:
    adding to said mold a second feedstock comprising an agglomerated metal powder and an agglomeration agent;
    forming said second feedstock into a dense portion; and
    removing said agglomeration agent of said formed second feedstock.

7. The method of claim 1, wherein the step of forming comprises die compression, cold isostatic pressing, hot isostatic pressing, metal injection molding, high velocity compaction or uniaxial pressing.

8. The method of claim 1, wherein said agglomerated metal powder comprises titanium, Ti-6Al-4V alloy, stainless steel or cobalt chrome.

9. The method of claim 1, wherein the agglomeration agent is polyethylene glycol.

10. The method of claim 1, wherein both the clusters and space filling material have a size of 250 µm or less.

11. The method of claim 1, wherein upon the step of forming the porous portion-, the clusters of the first feedstock create interconnected eggshell structures around the space filling material.

12. The method of claim 1, wherein the removing step includes leeching said agglomeration agent with a solvent and said space filling material with a solvent.

13. The method of claim 1, wherein after the removing step, the method further comprises sintering the brown state article.

* * * * *